United States Patent
Melton et al.

(10) Patent No.: US 10,253,298 B2
(45) Date of Patent: *Apr. 9, 2019

(54) METHODS FOR GENERATING STEM CELL-DERIVED BETA CELLS AND METHODS OF USE THEREOF

(71) Applicant: President and Fellows of Harvard College, Cambridge, MA (US)

(72) Inventors: Douglas A. Melton, Lexington, MA (US); Mads Gürtler, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/975,457

(22) Filed: Dec. 18, 2015

(65) Prior Publication Data

US 2016/0177269 A1 Jun. 23, 2016

Related U.S. Application Data

(60) Provisional application No. 62/093,974, filed on Dec. 18, 2014.

(51) Int. Cl.
| | |
|---|---|
| C12N 5/02 | (2006.01) |
| C12N 5/00 | (2006.01) |
| C12N 5/071 | (2010.01) |
| A61K 35/39 | (2015.01) |
| G01N 33/50 | (2006.01) |

(52) U.S. Cl.
CPC ............ *C12N 5/0678* (2013.01); *A61K 35/39* (2013.01); *C12N 5/0676* (2013.01); *G01N 33/507* (2013.01); *C12N 2501/16* (2013.01); *C12N 2501/727* (2013.01)

(58) Field of Classification Search
CPC .................................................. C12N 5/0678
See application file for complete search history.

(56) References Cited

U.S. PATENT DOCUMENTS

| | | | |
|---|---|---|---|
| 6,436,704 B1 | 8/2002 | Roberts et al. |
| 6,667,176 B1 | 12/2003 | Funk et al. |
| 6,800,480 B1 | 10/2004 | Bodnar et al. |
| 7,033,831 B2 | 4/2006 | Fisk et al. |
| 7,157,278 B2 | 1/2007 | Jin |
| 7,297,539 B2 | 11/2007 | Mandalam et al. |
| 7,326,572 B2 | 2/2008 | Fisk et al. |
| 7,410,798 B2 | 8/2008 | Mandalam et al. |
| 7,432,104 B2 | 10/2008 | Mitalipova et al. |
| 7,510,876 B2 | 3/2009 | D'amour et al. |
| 7,534,608 B2 | 5/2009 | Martinson et al. |
| 7,541,185 B2 | 6/2009 | D'amour et al. |
| 7,625,753 B2 | 12/2009 | Kelly et al. |
| 7,695,963 B2 | 4/2010 | Agulnick et al. |
| 7,695,965 B2 | 4/2010 | Martinson et al. |
| 7,704,738 B2 | 4/2010 | D'amour et al. |
| 7,964,402 B2 | 6/2011 | Terskikh et al. |
| 7,985,585 B2 | 7/2011 | D'amour et al. |
| 7,993,916 B2 | 8/2011 | Agulnick et al. |
| 7,993,920 B2 | 8/2011 | Martinson et al. |
| 8,008,075 B2 | 8/2011 | Green et al. |
| 8,129,182 B2 | 3/2012 | D'amour et al. |
| 8,153,429 B2 | 4/2012 | Robins et al. |
| 8,187,878 B2 | 5/2012 | Dalton et al. |
| 8,211,699 B2 | 7/2012 | Robins et al. |
| 8,216,836 B2 | 7/2012 | D'amour et al. |
| 8,278,106 B2 | 10/2012 | Martinson et al. |
| 8,334,138 B2 | 12/2012 | Robins et al. |
| 8,338,170 B2 | 12/2012 | Kelly et al. |
| 8,415,153 B2 | 4/2013 | Majumdar et al. |
| 8,445,273 B2 | 5/2013 | Green et al. |
| 8,603,811 B2 | 12/2013 | D'amour et al. |
| 8,623,645 B2 | 1/2014 | D'amour et al. |
| 8,647,873 B2 | 2/2014 | D'amour et al. |
| 8,658,151 B2 | 2/2014 | Kelly et al. |
| 8,785,184 B2 | 7/2014 | Xu |
| 8,785,185 B2 | 7/2014 | Xu et al. |
| 8,859,286 B2 | 10/2014 | Agulnick et al. |
| 9,096,832 B2 | 8/2015 | Xu |
| 9,109,245 B2 | 8/2015 | Agulnick et al. |
| 9,186,381 B2 | 11/2015 | Zender et al. |
| 2001/0049130 A1 | 12/2001 | Spielberg |
| 2002/0094569 A1 | 7/2002 | Yu et al. |
| 2003/0138948 A1 | 7/2003 | Fisk et al. |
| 2004/0121460 A1 | 6/2004 | Lumelsky et al. |
| 2004/0191901 A1 | 9/2004 | Assady et al. |
| 2004/0259244 A1 | 12/2004 | Scharp et al. |
| 2005/0053588 A1 | 3/2005 | Yin |

(Continued)

FOREIGN PATENT DOCUMENTS

| | | |
|---|---|---|
| EP | 1676574 A2 | 7/2006 |
| EP | 1456356 B1 | 12/2009 |

(Continued)

OTHER PUBLICATIONS

Greggio (2013, Development, 140:4452-4462).*
Non-Final Office Action from U.S. Appl. No. 14/975,421, dated Sep. 15, 2016.
Basford, et al., "The Functional and molecular Characterisation of Human Embryonic Stem Cell-Derived Insulin-Positive Cells Compared with Adult Pancreatic Beta Cells," *Diabetologia*, 55:358-371, (2012).
Corkey, et al., "A Role for Malonyl-CoA in Glucose-Stimulated Insulin Secretion from Clonal Pacreatic β-Cells," *J. Biol. Chem.*, 254(36):21608-21612, (Dec. 1989).
Lim, et al., Microencapsulated Islets as Bioartificial Endocrine Pancreas, *Science*, 210(4472):908-910, (Nov. 21, 1980).
Phillips, et al., "Directed Differentiation of Human Embryonic Stem Cells into the Pancreatic Endocrine Lineage," *Stem Cells and Dev.*, 16:561-578, (2007).

(Continued)

*Primary Examiner* — Valarie E Bertoglio
(74) *Attorney, Agent, or Firm* — Morse, Barnes-Brown & Pendleton, P.C.; Lisa M. Warren, Esq.

(57) ABSTRACT

Disclosed herein are methods for generating SC-β cells, and isolated populations of SC-β cells for use in various applications, such as cell therapy.

11 Claims, 4 Drawing Sheets

(56) References Cited

U.S. PATENT DOCUMENTS

| | | |
|---|---|---|
| 2006/0040385 A1 | 2/2006 | Itskovitz-Eldor et al. |
| 2006/0040387 A1 | 2/2006 | Fisk et al. |
| 2006/0194321 A1 | 8/2006 | Colman et al. |
| 2008/0145889 A1 | 6/2008 | Fisk et al. |
| 2008/0299582 A1 | 12/2008 | Mandalam et al. |
| 2009/0170198 A1 | 7/2009 | Rezania |
| 2009/0263896 A1 | 10/2009 | Kelly et al. |
| 2009/0325180 A1 | 12/2009 | Fisk et al. |
| 2010/0015100 A1 | 1/2010 | Xu |
| 2010/0015711 A1 | 1/2010 | Davis et al. |
| 2010/0144033 A1 | 6/2010 | Mandalam et al. |
| 2010/0240130 A1 | 9/2010 | Majumdar et al. |
| 2010/0311166 A1 | 12/2010 | Florio et al. |
| 2011/0014702 A1 | 1/2011 | Xu |
| 2011/0053930 A1 | 3/2011 | Yu et al. |
| 2011/0151560 A1 | 6/2011 | Xu |
| 2011/0280842 A1 | 11/2011 | Melton et al. |
| 2011/0281355 A1 | 11/2011 | Xu |
| 2012/0009675 A1 | 1/2012 | Martinson et al. |
| 2012/0052571 A1 | 3/2012 | Fryer |
| 2012/0052575 A1 | 3/2012 | Rezania |
| 2012/0052576 A1 | 3/2012 | Rezania |
| 2012/0135015 A1 | 5/2012 | Noguchi et al. |
| 2012/0141436 A1 | 6/2012 | Bonner-Weir et al. |
| 2013/0034526 A1 | 2/2013 | Itskovitz-Eldor et al. |
| 2013/0071931 A1 | 3/2013 | Ishikawa |
| 2013/0189777 A1 | 7/2013 | Rezania |
| 2013/0316357 A1 | 11/2013 | D'amour et al. |
| 2013/0330823 A1 | 12/2013 | Rezania |
| 2013/0337564 A1 | 12/2013 | Davis et al. |
| 2014/0080210 A1 | 3/2014 | Davis et al. |
| 2014/0134726 A1 | 5/2014 | D'amour et al. |
| 2014/0154801 A1 | 6/2014 | D'amour et al. |
| 2014/0154802 A1 | 6/2014 | Robins et al. |
| 2014/0162359 A1 | 6/2014 | Rezania |
| 2014/0186305 A1 | 7/2014 | Rezania |
| 2014/0186948 A1 | 7/2014 | Schulz et al. |
| 2014/0186953 A1 | 7/2014 | Rezania |
| 2014/0193902 A1 | 7/2014 | D'amour et al. |
| 2014/0193904 A1 | 7/2014 | D'amour et al. |
| 2014/0242693 A1 | 8/2014 | Fryer et al. |
| 2014/0287944 A1 | 9/2014 | Hrvatin et al. |
| 2014/0329704 A1 | 11/2014 | Melton et al. |
| 2014/0335611 A1 | 11/2014 | Chen et al. |
| 2015/0218522 A1 | 8/2015 | Peterson et al. |
| 2015/0240212 A1 | 8/2015 | Peterson et al. |
| 2015/0247123 A1 | 9/2015 | Ekberg et al. |
| 2015/0329828 A1 | 11/2015 | Rezania |
| 2105/0376574 | 12/2015 | Talavera-Adame et al. |
| 2016/0022742 A1 | 1/2016 | Zender et al. |
| 2016/0175363 A1 | 6/2016 | Melton et al. |
| 2016/0177267 A1 | 6/2016 | Melton et al. |
| 2016/0177268 A1 | 6/2016 | Melton et al. |
| 2016/0186143 A1 | 6/2016 | Melton et al. |
| 2016/0208215 A1 | 7/2016 | Doehn et al. |
| 2017/0029778 A1 | 2/2017 | Peterson et al. |
| 2017/0233700 A1 | 8/2017 | Kunisada et al. |
| 2017/0240866 A1 | 8/2017 | Wells et al. |

FOREIGN PATENT DOCUMENTS

| | | |
|---|---|---|
| EP | 2267116 A1 | 12/2010 |
| EP | 2283117 B1 | 2/2011 |
| EP | 2292734 A1 | 3/2011 |
| EP | 2341147 A2 | 6/2011 |
| EP | 2377922 A2 | 10/2011 |
| EP | 2569419 | 11/2011 |
| EP | 2650359 A1 | 10/2013 |
| EP | 2650360 A2 | 10/2013 |
| EP | 2664669 A1 | 11/2013 |
| EP | 2674485 A1 | 12/2013 |
| WO | WO 96/31242 | 10/1996 |
| WO | WO 1999/020740 A2 | 4/1999 |
| WO | WO 2001/088104 A2 | 11/2001 |
| WO | WO 2002/042445 A2 | 5/2002 |
| WO | WO 2003/050249 A2 | 6/2003 |
| WO | WO 03/10026 A2 | 12/2003 |
| WO | WO 2004/058764 A1 | 7/2004 |
| WO | WO 2007/002136 A2 | 1/2007 |
| WO | WO 2007/075807 A2 | 7/2007 |
| WO | WO 2007/103282 A2 | 9/2007 |
| WO | WO 2007/127927 A2 | 11/2007 |
| WO | WO 2008/083331 A2 | 7/2008 |
| WO | WO 2008/102000 A1 | 8/2008 |
| WO | WO 2009/012428 A2 | 1/2009 |
| WO | WO 2009/018453 A1 | 2/2009 |
| WO | WO 2009/070592 | 6/2009 |
| WO | WO 2010/057039 | 5/2010 |
| WO | WO 2010/059778 | 5/2010 |
| WO | WO 2011/079017 A9 | 6/2011 |
| WO | WO 2011/123572 A1 | 10/2011 |
| WO | WO 2012/020845 | 2/2012 |
| WO | WO 2012/021698 | 2/2012 |
| WO | WO 2012/025725 A1 | 3/2012 |
| WO | WO 2012/030540 A2 | 3/2012 |
| WO | WO 2012/168930 | 12/2012 |
| WO | WO 2013/057164 A1 | 4/2013 |
| WO | WO 2013/095953 A1 | 6/2013 |
| WO | WO 2014/033322 A1 | 3/2014 |
| WO | WO 2014/105543 A1 | 7/2014 |
| WO | WO 2014/105546 A1 | 7/2014 |
| WO | WO 2014/151871 A1 | 9/2014 |
| WO | WO 2014/160413 A1 | 10/2014 |
| WO | WO 2014/201167 A1 | 12/2014 |
| WO | WO 2015/002724 A1 | 1/2015 |
| WO | WO 2015/028614 A1 | 3/2015 |
| WO | WO 2015/175307 A1 | 11/2015 |
| WO | WO 2016/100898 A1 | 6/2016 |
| WO | WO 2016/100909 A1 | 6/2016 |
| WO | WO 2016/100921 A1 | 6/2016 |
| WO | WO 2016/100925 A1 | 6/2016 |
| WO | WO 2016/100930 A1 | 6/2016 |

OTHER PUBLICATIONS

Zhu, et al., "Generation of Pancreatic Insulin-Producing Cells from Rhesus Monkey Induced Pluripotent Stem Cells," *Diabetologia*, 54:2325-2336, (2011).

Supplementary European Search Report for European Application EP 14819763.5, dated Jan. 26, 2017.

Non-Final Office Action for U.S. Appl. No. 14/975,383, dated Feb. 1, 2017.

Non-Final Office Action for U.S. Appl. No. 14/975,421, dated Mar. 1, 2017.

Non-Final Office Action for U.S. Appl. No. 14/684,129, dated May 8, 2017.

Non-Final Office Action for U.S. Appl. No. 14/684,101, dated Jun. 1, 2017.

Extended European Search Report for European Application EP 14819763.5, dated May 23, 2017.

Apelqvist et al., "Notch Signaling Controls Pancreatic Cell Differentiation," *Nature*, 400:877-881, (1999).

Aguayo-Mazzucato et al., "Thyroid Hormone Promotes Postnatal Rat Pancreatic β-Cell Development and Glucose-Responsive Insulin Secretion Through MAFA," *Diabetes*, 62:1569-580, (2013).

Ashery-Padan et al., "Conditional inactivation of Pax6 in the pancreas causes early onset of diabetes," *Developmental Biology*, 269:479-488, (2004).

Assady et al., "Insulin Production by Human Embryonic Stem Cells," *Diabetes*, 50:1691-1697, (Aug. 2001).

Baetge et al., "Production of β-cells from human embryonic stem cells," *Diabetes, Obesity and Metabolism*, 10:186-194, (2008).

Beattie et al., "Sustained Proliferation of PDX-1+ Cells Derived From Human Islets," *Diabetes*, 48: 1013-1019, (May 1999).

Bellin et al., "Potent induction immunotherapy promotes long-term insulin independence after islet transplantation in type 1 diabetes," *Am. J. Transplant.*, 12:1576-1583, (2012).

Boretti et al., "Induced cell clustering enhances islet beta cell formation from human cultures enriched for pancreatic ductal epithelial cells," *Tissue Eng.*, 12(4):939-948, (2006).

(56) References Cited

OTHER PUBLICATIONS

Boretti et al., "Induced cell clustering enhances islet beta cell formation from human cultures enriched for pancreatic ductal epithelial cells," *2003 Summer Bioengineering Conference*, Jun. 25-29, Sonesta Beach Resport in Key Biscayne, Florida, 2 pages.
Bose et al., "Human embryonic stem cell differentiation into insulin secreting beta-cells for diabetes," *Cell Biol Int.*, 36(11):1013-1020, (2012).
Brolen et al., "Signals From the Embryonic Mouse Pancreas Induce Differentiation of Human Embryonic Stem Cells Into Insulin-Producing β-cell-like Cells," *Diabetes*, 54:2867-2874, (2005).
Cerf, "Transcription factors regulating β-cell function," *European Journal of Endocrinology*, 155:671-679, (2006).
Chakrabarti et al., "Transcription factors direct the development and function of pancreatic beta cells," *Trends Endocrinol Metab.*, 14(2):78-84, (Mar. 2003).
Chen et al., "Scalable GMP complain suspension culture system for human ES cells," *Stem Cell Research*, 8:388-402, (2012).
Cheng et al., "Self-renewing endodermal progenitor lines generated from human pluripotent stem cells," *Cell Stem Cell*, 10:371-384, (2012).
Chiang et al., "Single-cell transcript analysis of pancreas development," *Dev. Cell.*, 4(3):383-93, (Mar. 2003).
Choi et al., "A comparison of genetically matched cell lines reveals the equivalence of human iPSCs and ESCs," *Nat. Biotechnol.*, Oct. 26. 2015. doi: 10.1038/nbt.3388. [Epub ahead of print].
Cohen et al., "Antibiotics reduce the growth rate and differentiation of embryonic stem cell cultures," *Tissue Eng.*, 12(7):2025-2030, (2006).
D'Amour et al., "Production of pancreatic hormone-expressing endocrine cells from human embryonic stem cells," *Nat. Biotechnol.*, 24(11):1392-1401, (2006).
D'Amour et al., "Efficient differentiation of human embryonic stem cells to definitive endoderm," *Nat. Biotechnol.*, 23(12):1534-1541, (2005).
Dror et al., "Notch Signaling Suppresses Apoptosis in Adult Human and Mouse Pancreatic Islet Cells," *Diabetlogia* 50:2504-2515, (2007).
Eberhardt et al., "Multipotential nestin and lsl-1 positive mesenchymal stem cells isolated from human pancreatic islets," *Biochem. Biophys. Res. Commun.*, 345(3):1167-76, (2006).
Habener et al., "Minireview: Transcriptional Regulation in Pancreatic Development," *Endocrinology*, 146(3):1025-1034, (2004).
Haycock, "3D Cell Culture: A Review of Current Approaches and Techniques," *Molecular Biology*, 695:1-15, (2011).
Heremans et al., "Recapitulation of embryonic neuroendocrine differentiation in adult human pancreatic duct cells expressing neurogenin 3," *The Journal of Cell Biology*, 159(2):303-311, (Oct. 2002).
Hernandez et al., "Microcapsules and microcarriers for in situ cell delivery," *Advanced Drug Delivery Reviews*, 62:711-730, (2010).
Hrvatin et al., "Differentiated human stem cells resemble fetal, not adult, β-cells," *PNAS*, 111(8):3038-3043, (2014).
Isayeva et al., "Characterization and performance of membranes designed for macroencapsulation/implantation of pancreatic islet cells," *Biomaterials*, 24(20):3483-3491, (2003).
Jahansouz et al., "Evolution of β-Cell Replacement Therapy in Diabetes Mellitus: Islet Cell Transplantation," *Journal of Transplantation*, pp. 1-21, (2011).
Jeon et al., "Differentiation and Transplantation of Functional Pancreatic Beta Cells Generated from Induced Pluripotent Stem Cells Derived from a Type 1 Diabetes Mouse Model," *Stem Cells Dev.*, 21(14):2642-2655, (2012).
Jiang et al., "In vitro Derivation of Functional Insulin-Producing Cells from Human Embryonic Stem Cells," *Cell Research*, 17(4):333-344, (2007).
Kroon et al., "Pancreatic endoderm derived from human embryonic stem cell generates glucose-responsive insulin-secreting cells in vivo," *Nat. Biotechnol.*, 26(4):443-452, (Apr. 2008).

Kumar et al., "Signals from lateral plate mesoderm instruct endoderm toward a pancreatic fate," *Dev. Biol.*, 259(1):109-22, (Jul. 2003).
Kumar et al.,"Recent Developments in β-Cell Differentiation of Pluripotent Stem Cells Induced by Small and Large Molecules," *Int. J. Mol. Sci.*, 15(12):23418-23447, (2014).
Lee et al., "All-Trans-Retinoic Acid as a Novel Therapeutic Strategy for Alzheimer's Disease," *Expert Rev. Neurother*, 9(11):1615-1621, (2009).
Lumelsky et al., "Differentiation of Embryonic Stem Cells to Insulin-Secreting Structures Similar to Pancreatic Islets," *Science*, 292:1389-1394, (2001).
Madsen et al., "Towards cell therapy for diabetes," *Nat. Biotechnol.*, 24(12):1481-1483, (Dec. 2006).
Maehr et al., "Generation of pluripotent stem cells from patients with type 1 diabetes," *PNAS*, 106(37):15768-15773, (2009).
Marzorati et al., "Culture Medium Modulates Proinflammatory Conditions of Human Pancreatic Islets Before Transplantation," *Am. J. Transplant*, 6(11):2791-2795, (2006).
Matschinsky, "Assessing the potential of glucokinase activators in diabetes therapy," *Nature Reviews Drug Discovery*, 8:399-416, (2009).
McLean et al., "Activin A efficiently specifies definitive endoderm from human embryonic stem cells only when phosphatidylinositol 3-kinase signaling is suppressed," *Stem Cells*, 25(1):29-38, (Jan. 2007).
Michael et al., "Pacreatic β-cells secrete insuling in fast- and slow-release forms," *Diabetes*, 55: 600-607, (2006).
Moens et al., "Dual glucagon recognition by pancreatic beta-cells via glucagon and glucagon-like peptide 1 receptors," *Diabetes*, 47:66-72, (1998).
Mollard et al., "Design, Synthesis, and Biological Evaluation of a Series of Novel AXL Kinase Inhibitors," *ACS Medicinal Chemistry Letters*, 2:907-912, (2011).
Motté et al., "Composition and function of macroencapsulated human embryonic stem cell-derived implants: comparison with clinical human islet cell grafts," *American Journal of Physiology-Endocrinology and Metabolism*, 307(9):E838-E846, (2004).
Mudduluru et al., "Regulation of Axl receptor tyrosine kinase expression by miR-34a and miR-199a/b in solid cancer," *Oncogene*, 30(25):2889-2899, (2011).
Murua et al., "Cell microencapsulation technology: Towards clinical application," *Journal of Controlled Release*, 132(2):76-83, (2008).
Narayanan et al., "Extracellular Matrix-Mediated Differentiation of Human Embryonic Stem Cells: Differentiation to Insulin-Secreting Beta Cells," *Tissue Engineering: Part A*, 20(1-2):424-433, (2013).
Nostro et al., "Stage-specific signaling through TGFβ family members and WNT regulates patterning and pancreatic specification of human pluripotent stem cells," *Development*, 138:861-871, (2011).
O'Brien et al.,"Suspended in culture—Human pluripotent cells for scalable technologies," *Stem Cell Research*, 9:167-170, (2012).
Orive et al., "Application of cell encapsulation for controlled delivery of biological therapeutics," *Advanced Drug Delivery Reviews*, pp. 1-12, (2013).
Pagliuca et al., "Generation of functional human pancreatic β cells in vitro," *Cell*, 159(2):428-39, (Oct. 2014).
Pagliuca et al., "How to make a functional β-cell," *Development*, 140:2472-2483, (2013).
Parsons et al., "Notch-Responsive Cells Initiate the Secondary Transition in Larval Zebrafish Pancreas," *Mechanisms of Development*, 126(10):898-912, (2009).
Qi et al., "PVA hydrogel sheet macroencapsulation of the bioartificial pancreas," *Biomaterials*, 24(27):5885-5892, (2004).
Ratanasavanh et al., "Immunocytochemical evidence for the maintenance of cytochrome P-450 isozymes, NADPH cytochrome C reductase, and epoxide hydrolase in pure and mixed primary cultures of adult human hepatocytes," *J. Histochem. Cytochem.*, 34(4):527-33, (Apr. 1986).
Rathaore et al., "Microencapsulation of Microbial cells," *Journal of Food Engineering*, 116:369-381, (2013).
Ravassard et al., "A genetically engineered human pancreatic β cell line exhibiting glucose-inducible insulin secretion," *The Journal of Clinical Investigation*, 121(9):3589-3597, (2011).

(56) References Cited

OTHER PUBLICATIONS

Rezania et al., "Maturation of human embryonic stem cell-deprived pancreatic progenitors into functional islets capable of treating pre-existing diabetes in mice," Diabetes, 61:2016-2029, (2012).
Rezania et al., "Production of functional glucagon-secreting α-cells from human embryonic stem cells," Diabetes, 60:239-247, ( Jan. 2011).
Rezania et al., "Reversal of diabetes with insulin-producing cells derived in vitro from human pluripotent stem cells," Nat. Biotechnol., 21(11):1121-1133, (Nov. 2014).
Roche, "Protocols to differentiate embryonic stem cells into insulin producing cells," Av. Diabetol., 24(2):128-137, (2008).
Rovira et al., "Chemical Screen Identifies FDA-Approved Drugs and Target Pathways That Induce Precocious Pancreatic Endocrine Differentiation," Proc. Natl. Acad. Sci. U.S.A., 108(48):19264-19269, (2011).
Sander et al., "Homeobox gene Nkx6.1 lies downstream of Nkx2.2 in the major pathway of β-cell formation in the pancreas," Development, 127:5533-5540, (2000).
Sander et al., "The β-cell transcription factors and development of the pancreas," J. Mol. Med., 75:327-340, (1997).
Schuldiner et al., "Effects of eight growth factors on the differentiation of cells derived from human embryonic stem cells," Proc. Natl. Acad. Sci. U.S.A., 97(21):11307-11312, (Oct. 2000).
Schulz et al., "A scalabe system for production of functional pancreatic progenitors from human embryonic stem cells," PLoS One, 7(5):1-17, (May 2012).
Segrev et al., "Differentiation of Human Embryonic Stem Cells into Insulin-Producing Clusters," Stem Cells, 22:265-274, (2004).
Shaer et al., "Differentiation of human-induced pluripotent stem cells into insulin-producing clusters," Exp. Clin. Transplant, 13(1):68-75, (2014).
Shapiro et al., "International trial of the Edmonton protocol for islet transplantation," N. Engl. J. Med., 355:1318-330, (2006).
Shi et al., "Inducing Embryonic Stem Cells to Differentiate into Pancreatic β-cells by a Novel Three-Step Approach with Activin A and All-Trans Retinoic Acid," Stem Cells 23:656-662 (2005).
Shim et al., "Directed differentiation of human embryonic stem cells towards a pancreatic cell fate," Diabetologia, 50:1128-1238, (2007).
Sneddon et al., "Self-renewal of embryonic-stem-cell-derived progenitors by organ-matched mesenchyme," Nature, 491:765-768, (2012).
SoRelle et al., "Beta Cell Replacement Therapy," Type 1 Diabetes—Pathogenesis, Genetics and Immunotherapy, 22:503-526, (2011).
Soria, "In-vitro differentiation of pancreatic β-cells," Differentiation, 68:205-219, (2001).
Spence et al., "Sox17 regulates organ lineage segregation of ventral foregut progenitor cells," Dev. Cell., 17(1):62-74, (Jul. 2009).
Taylor et al., "NKX6-I Is Essential for Maintaining the Functional State of Pancreatic Beta Cells," Cell Rep, 4:1262-275, (2013).
Thatava et al., "Indolactam V/GLP-1-mediated Differentiation of Human iPS Cells into Glucose-Responsive Insulin-Secreting Progeny," Gene Ther., 18(3):283-293, (2011).
Thowfeequ et al., "Betacellulin inhibits amylase and glucagon production and promotes beta cell differentiation in mouse embryonic pancreas," Diabetologia, 50:1688-1697, (2007).
Treff et al., "Differentiation of Embryonic Stem Cells Conditionally Expressing Neurogenin 3," Stem Cells, 24(11):2529-37, (1999).
Tsuchida et al., "Activin signaling as an emerging target for therapeutic interventions," Cell Communication & Signaling, 7(15):1-11, (2009).
Falzacappa et al., "3,5,3'-triiodothyronine (T3) is a survival factor for pancreatic beta-cells undergoing apoptosis," J. Cell Physiol., 206(2):309-321, (Feb. 2006).
Xie et al., "Dynamic chromatin remodeling mediated by polycomb proteins orchestrates pancreatic differentiation of human embryonic stem cells," Cell Stem Cell, 12:224-237, (2013).
Zanin et al., "The development of encapsulated cell technologies as therapies for neurological and sensory diseases," Journal of Controlled Release, 160:3-13, (2012).

Zhu et al., "Preventive Effect of Notch Signaling Inhibition by a γ-Secretase Inhibitor on Peritoneal Dialysis Fluid-induced Peritoneal Fibrosis in Rats," American Journal of Pathology, 176(2):650-659, (2010).
Zulewski, "Stem Cells with potential to generate insulin-producing cells in man," Swiss Med. Wkly, 136:647-654, (2006).
Zweigerdt et al., "Scalable expansion of human pluripotent stem cells in suspension culture," Nature Protocols, 6(5):689-700, (2011).
International Search Report for International Application PCT/US2014/041988, dated Dec. 24, 2014.
International Search Report for International Application PCT/US2014/041992, dated Oct. 24, 2014.
International Search Report for International Application PCT/US2015/066900, dated Mar. 3, 2016.
International Search Report for International Application PCT/US2015/066888, dated Feb. 26, 2016.
International Search Report for International Application PCT/US2015/066881, dated Mar. 3, 2016.
International Search Report for International Application PCT/US2015/066858, dated Mar. 11, 2016.
International Search Report for International Application PCT/US2015/066840, dated Mar. 31, 2016.
Non-Final Office Action for U.S. Appl. No. 14/684,129, dated Sep. 4, 2015.
Final Office Action for U.S. Appl. No. 14/684,129, dated Mar. 8, 2016.
Non-Final Office Action for U.S. Appl. No. 14/684,101, dated Aug. 25, 2015.
Final Office Action for U.S. Appl. No. 14/684,101, dated Jan. 28, 2016.
Kunisada et al., "Small molecules induce efficient differentiation into insulin-producing cells from human induced pluripotent stem cells," Stem Cell Research, 8:274-284, (2012).
Lin et al., "Transforming Growth Factor-β/Smad3 Signaling Regulates Insulin Gene Transcription and Pancreatic Islet β-Cell Function," The Journal of Biological Chemistry, 284(18):12246-12257, (May 1, 2009).
Nostro et al., "Generation of beta cells from human pluripotent stem cells: Potential for regenerative medicine," Seminars in Cell & Developmental Biology, 23:701-710, (2012).
Rezania et al., "Enrichment of Human Embryonic Stem Cell-Derived NKX6.1-Expressing Pancreatic Progenitor Cells Accelerates the Maturation of Insulin-Secreting Cells in Vivo," Stem Cells, 31:2432-2442, (2013).
ThermoFisher Scientific, "B-27 Serum-Free Supplement (50X) liquid," ThermoFisher Scientific Website, Retrieved from the Internet: URL:https://www.thermofisher.com/nl/en/home/technical-resources/media-formulation.250.html, on Jun. 13, 2016.
Wachs et al., "High Efficacy of Clonal Growth and Expansion of Adult Neural Stem Cells," Laboratory Investigation, 83(7):949-962, (Jul. 2003).
Supplementary European Search Report for European Application EP 14 81 0778, dated Sep. 28 2016.
Advisory Action Before the Filing of an Appeal Brief for U.S. Appl. No. 14/684,101, dated Sep. 1, 2016.
Advisory Action Before the Filing of an Appeal Brief for U.S. Appl. No. 14/684,129, dated Nov. 9, 2016.
Final Office Action for U.S. Appl. No. 14/684,129, dated Mar. 9, 2018.
Final Office Action for U.S. Appl. No. 14/684,101, dated Jan. 16, 2018.
Bennett, et al., "SP600125, An Anthrapyrazolone Inhibitor of Jun N-Terminal Kinase," PNAS, 98(24):13681-13686, (Nov. 20, 2001).
CMRL-1066 Data Sheet. Retrieved online Sep. 30, 2017. https://www.sigmaaldrich.com/content/dam/sigma-aldrich/docs/sigma/datasheet/c0422dat.pdf (1998).
Docherty, "Pancreatic Stellate Cells Can Form New β-Like Cells," Biochem, J., 421:e1-e4, (2009).
Huynh, et al., "Screening and Identification of a Novel Class of TGF-β Type 1 Receptor Kinase Inhibitor," Society for Laboratory Automation and Screening, 16(7):724-733, (2011).

(56) References Cited

OTHER PUBLICATIONS

Nishimura, et al., "A Switch from MafB to MafA Expression Accompanies Differentiation to Pancreatic β-Cells," *Developmental Biology*, 293:526-539, (2006).

Piran, et al., "Pharmacological Induction of Pancreatic Islet Cell Transdifferentiation; Relevance to Type I Diabetes," *Cell Death and Disease*, 5(e1357):1-36, (2014).

Tsaniras, et al., "Generating Pancreatic β-Cells from Embryonic Stem Cells by Manipulating Signaling Pathways," Journal of Endocrinology, 206:13-26, (2010).

Non-Final Office Action for U.S. Appl. No. 14/975,255, dated Jul. 17, 2017.

Non-Final Office Action for U.S. Appl. No. 14/975,158, dated Sep. 13, 2017.

Non-Final Office Action for U.S. Appl. No. 14/898,015, dated Oct. 13, 2017.

Campbell-Thompson, et al., "Collection Protocol for Human Pancreas," *Journal of Visualized Experiments*, 63:1-5, (May 2012).

Hanley, "Closing in on Pancreatic Beta Cells," *Nature Biotechnology*, 32(11):1100-1102, (Nov. 2014).

Shahjalal, et al., "Generation of Insulin-Producing β-Like Cells from Human iPS Cells in a Defined and Completely Xeno-Free Culture System," *Journal of Molecular Cell Biology*, 6(5):394-408, (Oct. 2014).

Final Office Action for U.S. Appl. No. 14/975,158, dated Jun. 28, 2018.

Non-Final Office Action for U.S. Appl. No. 14/975,255, dated Apr. 12, 2018.

Notice of Allowance for U.S. Appl. No. 14/684,101, dated May 4, 2018.

Final Office Action for U.S. Appl. No. 14/898,015, dated Aug. 10, 2018.

Notice of Allowance for U.S. Appl. No. 14/975,255, dated Sep. 6, 2018.

\* cited by examiner

METHODS FOR GENERATING STEM CELL-DERIVED BETA CELLS AND METHODS OF USE THEREOF

RELATED APPLICATIONS

This application claims the benefit of U.S. Provisional Application Ser. No. 62/093,974 filed on Dec. 18, 2014, the entire teachings of which are incorporated herein by reference.

BACKGROUND OF THE INVENTION

Diabetes affects more than 300 million people worldwide according to the International Diabetes Federation. Type 1 diabetes and type 2 diabetes involve 1 cell destruction and/or β cell dysfunction. Diabetic patients, particularly those suffering from type 1 diabetes, could potentially be cured through transplantation of β cells. While cadaveric human islet transplantation can render patients insulin independent for 5 years or longer, such approach is limited due to the scarcity and quality of donor islets (Bellin et al., 2012). Generating an unlimited supply of human β cells from stem cells could provide therapy to millions of patients as only a single cell type, the β cell, likely needs to be produced, and the mode of delivery is well understood: transplantation to a vascularized location within the body with immunoprotection. In addition, screening to identify novel drugs that improve β cell function, survival, or proliferation is also delayed due to limited islet supply and variability resulting from different causes of death, donor genetics, and other aspects in their isolation. As such, a steady, uniform supply of stem-cell-derived β cells would offer a useful drug discovery platform for diabetes. Moreover, genetically diverse stem-cell-derived β cells could be used for disease modeling in vitro or in vivo.

SUMMARY OF THE INVENTION

There is a need for methods of generating stem cell-derived β (SC-β) cells. The present invention is directed toward solutions to address this need, in addition to having other desirable characteristics.

In accordance with an embodiment of the present invention, a method for generating stem cell-derived β (SC-β) cells is provided. The method includes contacting a cell population with agents to direct differentiation to SC-β cells under conditions that promote cell clustering with additional agents comprising one or more of a) an effective amount of an agent that decreases the level and/or activity of rho-associated protein kinase (Rock) while the cell population comprises i) FOXA2+, SOX2+ primitive foregut cells differentiating to PDX1+ pancreatic progenitor cells, ii) PDX1+ pancreatic progenitor cells differentiating into PDX1+, NKX6.1+ pancreatic progenitor cells, and/or iii) PDX1+, NKX6.1+ pancreatic progenitor cells differentiating to chromogranin A, NKX6.1+ endocrine progenitor cells; b) an effective amount of Activin A while the cell population comprises PDX1+ pancreatic progenitor cells differentiating to PDX1+, NKX6.1+ pancreatic progenitor cells; and c) an effective amount of staurosporine while the cell population comprises PDX1−, NKX6.1+ pancreatic progenitor cells differentiating to chromogranin A, NKX6.1+ endocrine progenitor cells, thereby generating SC-β cells.

In accordance with aspects of the present invention, the method further comprises optionally washing the cell population after the PDX1+ pancreatic progenitor cells have differentiated to PDX1+, NKX6.1+ pancreatic progenitor cells to remove Activin A from contact with the cell population before contacting the cell population with staurosporine.

In accordance with aspects of the present invention, the agent comprises Y-27632. In accordance with aspects of the present invention, the effective amount of the agent comprises a concentration of 10 µM.

In accordance with aspects of the present invention, the effective amount of Activin A comprises a concentration of 5 ng/ml. In accordance with aspects of the present invention, the effective amount of staurosporine comprises a concentration of 3 nM.

In accordance with aspects of the present invention, the cell population comprising PDX1+ pancreatic progenitor differentiating to PDX1+, NKX6.1+ pancreatic progenitor cells is exposed to the agent and Activin A for a period of 6 days.

In accordance with aspects of the present invention, between at least between 75% and 80% of the cell population differentiates to chromogranin A, NKX6.1+ endocrine progenitor cells before differentiating to SC-β cells.

In accordance with aspects of the present invention, the agent i) prevents or minimizes cell cluster disintegration, ii) promotes cell survival, iii) increases cell cluster size, and combinations thereof.

In accordance with an embodiment of the present invention, an isolated SC-β cell or population thereof that exhibits a glucose stimulated insulin secretion (GSIS) response both in vitro and in vivo is provided. In accordance with aspects of the present invention, the isolated SC-β cell or population thereof exhibits a stimulation index that is at least between 1.0 and 3.0. In accordance with aspects of the present invention, the isolated SC-β cell or population thereof produces between approximately 300 uIU and 4000 uIU per 30 minute incubation at a high glucose concentration.

In accordance with an embodiment of the present invention, a microcapsule comprising the isolated SC-β cell or population thereof encapsulated therein is provided.

In accordance with an embodiment of the present invention, a macroencapsulation device comprising the isolated SC-β cell or population thereof encapsulated therein is provided.

In accordance with an embodiment of the present invention, a cell line comprising isolated SC-β cells that stably express insulin is provided.

In accordance with an embodiment of the present invention, assays comprising the isolated SC-β cell, or population thereof, or the cell line are provided. The assays can be used for: i) identifying one or more candidate agents which promote or inhibit a β cell fate selected from the group consisting of β cell proliferation, β cell replication, β cell death, β cell function, β cell susceptibility to immune attack, and β cell susceptibility to dedifferentiation or differentiation; or ii) identifying one or more candidate agents which promote the differentiation of at least one insulin-positive endocrine cell or a precursor thereof into at least one SC-β cell.

In accordance with an embodiment of the present invention, a method for the treatment of a subject in need thereof is disclosed. The method includes administering to a subject in need thereof i) an isolated population of SC-β cells, ii) a microcapsule comprising SC-β cells encapsulated therein; and/or iii) a macroencapsulation device comprising the SC-β cells encapsulated therein. In accordance with an embodiment of the present invention, an isolated population of SC-β cells, a microcapsule comprising the isolated population of SC-β cells, and/or a macroencapsulation device comprising the isolated population of SC-β cells is used for administering to a subject in need thereof. In accordance with aspects of the invention, the subject has, or has an increased risk of developing diabetes or has, or has an increased risk of developing a metabolic disorder.

In accordance with an embodiment of the present invention, an artificial islet or pancreas comprising SC-β cells is provided.

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), Current Protocols in Molecular Biology, Current Protocols in Immunology, Current Protocols in Protein Science, and Current Protocols in Cell Biology, all John Wiley & Sons, N.Y., edition as of December 2008; Sambrook, Russell, and Sambrook, Molecular Cloning: A Laboratory Manual, 3rd ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange; 10th ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Institute of Genetic Medicine, Johns Hopkins University (Baltimore, Md.) and National Center for Biotechnology Information, National Library of Medicine (Bethesda, Md.), as of May 1, 2010, World Wide Web URL: http://www.ncbi.nlm.nih.gov/omim/ and in Online Mendelian Inheritance in Animals (OMIA), a database of genes, inherited disorders and traits in animal species (other than human and mouse), at http://omia.angis.org.au/contact.shtml. All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

BRIEF DESCRIPTION OF THE DRAWINGS

These and other characteristics of the present invention will be more fully understood by reference to the following detailed description in conjunction with the attached drawings. The patent or application file contains at least one drawing executed in color. Copies of this patent or patent application publication with color drawings will be provided by the Office upon request and payment of the necessary fee.

DETAILED DESCRIPTION OF THE INVENTION

Figure 1A:
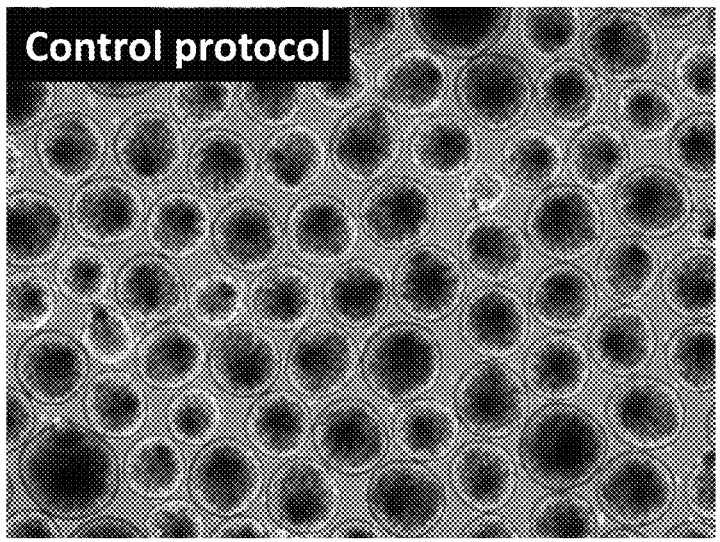
FIG. 1A and FIG. 1B are images of cells obtained using an exemplary control protocol for generating SC-β cells and cells obtained using a method for generating SC-β cells according to an embodiment of the present invention, respectively, demonstrating that the method for generating SC-β cells according to the present invention prevents or minimizes cell cluster disintegration, promotes cell survival, and increases cell cluster size and number.
Figure 1B:
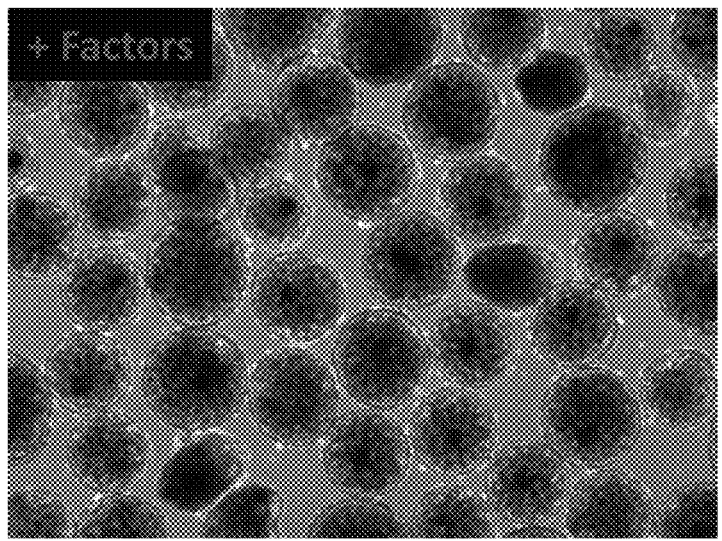
Figure 2A:
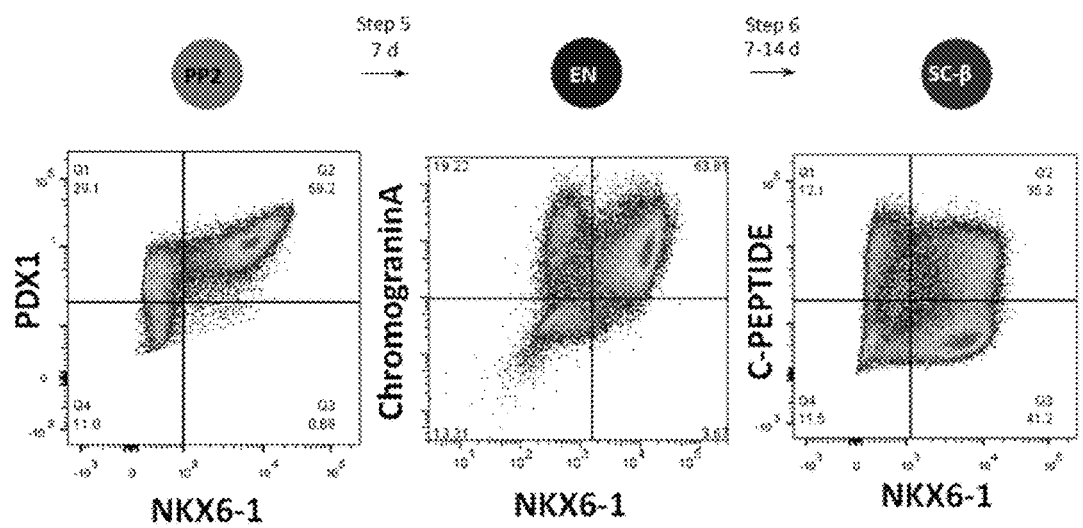
FIG. 2A are FACS plots demonstrating that the cells obtained at each differentiation stage (S4, S5, and S6) using a method for generating SC-β cells according to an embodiment of the present invention maintain marker expression.
Figure 2B:
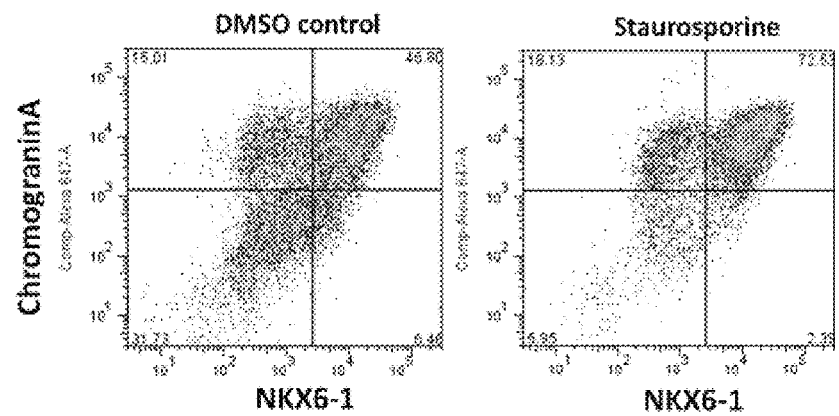
FIG. 2B are FACS plots of cells (e.g., SC-β cells) obtained using a control (e.g., DMSO) at the end of Step 6 (left panel) and cells (e.g., SC-β cells) obtained at the end of Step 6 of method for generating SC-β cells according to an embodiment of the present invention (right panel), demonstrating that staurosporine treatment generates a near pure endocrine population.
Figure 2C:
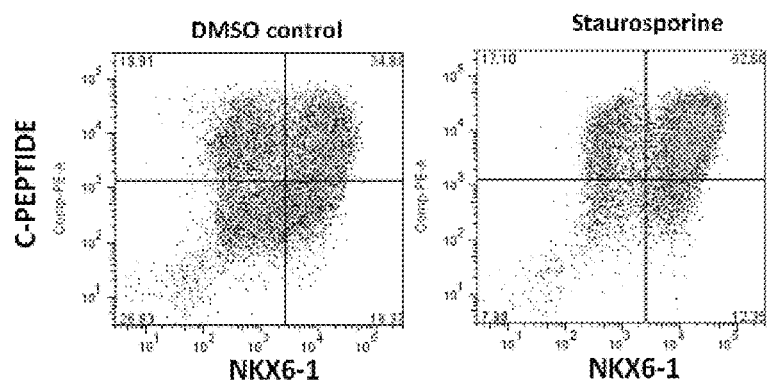
FIG. 2C are FACS plots of cells (e.g., SC-β cells) obtained using a control (e.g., DMSO) at the end of Step 6 (left panel) and cells (e.g., SC-β cells) obtained at the end of Step 6 of method for generating SC-β cells according to an embodiment of the present invention (right panel), demonstrating that staurosporine treatment generates a higher percentage of NKX6.1+, C-Peptide+ cells.

The present invention is directed to generating SC-β cells, in particular SC-β cells that exhibit in vitro and in vivo function. More particularly, work described herein demonstrates that contacting S2 cells, S3 cells, and S4 cells during Step 3, Step 4 and Step 5 with a Rock inhibitor with Activin A present during Step 4 in accordance with an embodiment of the present invention prevents or minimizes cell cluster disintegration, promotes cell survival, and increases the cell cluster size and number of cells in the resulting cell populations as compared to a control, as is shown in FIG. 1A (control) and FIG. 1B. Additionally, work described herein demonstrates that contacting S4 cells during Step 5 with staurosporine together with the Rock inhibitor and in the absence of Activin A generates cells that maintain marker expression as shown in FIG. 2A, as well as generates a near pure endocrine population as shown in FIG. 2B, and a higher percentage of NKX6.1+, C-Peptide+ cells as shown in FIG. 2C. The SC-β cells generated in accordance with the methods of the present invention can be used in various assays to identify novel drugs that improve β cell function, survival, or proliferation, cell therapies (e.g., for treating diabetes and/or metabolic disorders), and in the construction of artificial islets and/or an artificial pancreas.

Some Definitions

"Differentiation" is the process by which an unspecialized ("uncommitted") or less specialized cell acquires the features of a specialized cell such as, for example, a pancreatic cell. A differentiated cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. As used herein, the lineage of a cell defines the heredity of the cell, i.e., which cells it came from and to what cells it can give rise. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

As used herein, "markers", are nucleic acid or polypeptide molecules that are differentially expressed in a cell of interest. Differential expression means an increased level for a positive marker and a decreased level for a negative marker as compared to an undifferentiated cell. The detectable level of the marker nucleic acid or polypeptide is sufficiently higher or lower in the cells of interest compared to other cells, such that the cell of interest can be identified and distinguished from other cells using any of a variety of methods known in the art.

As used herein, a cell is "positive" or "+" for a specific marker (e.g., expresses the marker) when the specific marker is sufficiently detected in the cell. Similarly, the cell is "negative" or "−" for a specific marker when the specific marker is not sufficiently detected in the cell. For example, positive by FACS is usually greater than 2%, whereas the negative threshold by FACS is usually less than 1%.

Figure 3A:
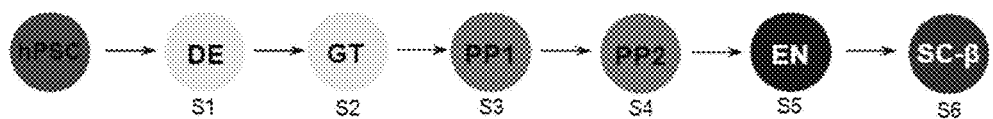
FIG. 3A is a schematic illustrating six stages of differentiation of human pluripotent stem cells to SC-β cells. hPSC=human pluripotent stem cell, DE=definitive endoderm cell, GT=gut tube cell, PP1=pancreatic progenitor cell 1, PP2=pancreatic progenitor cell 2, EN=endocrine progenitor cell, SC-β=stem cell-derived β cells.

The process of differentiating pluripotent stem cells into functional pancreatic endocrine cells (i.e., SC-β cells) in vitro may be viewed in some aspects as progressing through six consecutive stages, as is shown in the exemplary protocol depicted in FIG. 3A. In this step-wise progression, "Stage 1" or "S1" refers to the first step in the differentiation process, the differentiation of pluripotent stem cells into cells expressing markers characteristic of definitive endoderm cells ("DE", "Stage 1 cells" or "S1 cells"). "Stage 2" refers to the second step, the differentiation of cells expressing markers characteristic of definitive endoderm cells into cells expressing markers characteristic of gut tube cells ("GT", "Stage 2 cells" or "S2 cells"). "Stage 3" refers to the third step, the differentiation of cells expressing markers characteristic of gut tube cells into cells expressing markers characteristic of pancreatic progenitor 1 cells ("PP1", "Stage 3 cells" or "S3 cells"). "Stage 4" refers to the fourth step, the differentiation of cells expressing markers characteristic of pancreatic progenitor 1 cells into cells expressing markers characteristic of pancreatic progenitor 2 cells ("PP2", "Stage 4 cells" or "S4 cells"). "Stage 5" refers to the fifth step, the differentiation of cells expressing markers characteristic of pancreatic progenitor 2 cells into cells expressing markers characteristic of pancreatic endoderm cells and/or pancreatic endocrine progenitor cells ("EN", "Stage 5 cells" or "S5 cells"). "Stage 6" refers to the differentiation of cells expressing markers characteristic of pancreatic endocrine progenitor cells into cells expressing markers characteristic of pancreatic endocrine β cells ("SC-β cells", "Stage 6 cells" or "S6 cells"). It should be appreciated, however, that not all cells in a particular population progress through these stages at the same rate, i.e., some cells may have progressed less, or more, down the differentiation pathway than the majority of cells present in the population.

Characteristics of the various cell types associated with the stages shown in FIG. 3A are now described. "Definitive endoderm cells," as used herein, refers to cells which bear the characteristics of cells arising from the epiblast during gastrulation and which form the gastrointestinal tract and its derivatives. Definitive endoderm cells express at least one of the following markers: FOXA2 (also known as hepatocyte nuclear factor 3β ("HNF3β")), GATA4, SOX17, CXCR4, Brachyury, Cerberus, OTX2, goosecoid, C-Kit, CD99, and MIXL1, Markers characteristic of the definitive endoderm cells include CXCR4, FOXA2 and SOX17. Thus, definitive endoderm cells may be characterized by their expression of CXCR4, FOXA2 and SOX17. In addition, depending on the length of time cells are allowed to remain in Stage 1, an increase in HNF4a may be observed.

"Gut tube cells," as used herein, refers to cells derived from definitive endoderm that can give rise to all endodermal organs, such as lungs, liver, pancreas, stomach, and intestine. Gut tube cells may be characterized by their substantially increased expression of HNF4α over that expressed by definitive endoderm cells. For example, a ten to forty fold increase in mRNA expression of HNF4a may be observed during Stage 2.

"Pancreatic progenitor 1 cells," as used herein, refers to endoderm cells that give rise to the esophagus, lungs, stomach, liver, pancreas, gall bladder, and a portion of the duodenum. Pancreatic progenitor 1 cells express at least one of the following markers: PDX1, FOXA2, CDX2, SOX2, and HNF4α. Pancreatic progenitor 1 cells may be characterized by an increase in expression of PDX1, compared to gut tube cells. For example, greater than fifty percent of the cells in Stage 3 cultures typically express PDX1.

"Pancreatic progenitor 2 cells," as used herein, refers to cells that express at least one of the following markers: PDX1, NKX6.1, HNF6, NGN3, SOX9, PAX4, PAX6, ISL1, gastrin, FOXA2, PTF1a, PROX1 and HNF4α. Pancreatic progenitor 2 cells may be characterized as positive for the expression of PDX1, NKX6.1, and SOX9.

"Pancreatic endocrine progenitor cells" or "endocrine progenitor cells" are used interchangeably herein to refer to pancreatic endoderm cells capable of becoming a pancreatic hormone expressing cell. Pancreatic endocrine progenitor cells express at least one of the following markers; NGN3;

NKX2.2; NeuroD1; ISL1; PAX4; PAX6; or ARX. Pancreatic endocrine progenitor cells may be characterized by their expression of NKX2.2 and NeuroD1.

A "precursor thereof" as the term relates to a pancreatic endocrine progenitor cell refers to any cell that is capable of differentiating into a pancreatic endocrine progenitor cell, including for example, a pluripotent stem cell, a definitive endoderm cell, a gut tube cell, or a pancreatic progenitor cell, when cultured under conditions suitable for differentiating the precursor cell into the pancreatic pro endocrine cell.

"Pancreatic endocrine cells," as used herein, refer to cells capable of expressing at least one of the following hormones: insulin, glucagon, somatostatin, ghrelin, and pancreatic polypeptide. In addition to these hormones, markers characteristic of pancreatic endocrine cells include one or more of NGN3, NeuroD1, ISL1, PDX1, NKX6.1, PAX4, ARX, NKX2.2, and PAX6. Pancreatic endocrine cells expressing markers characteristic of β cells can be characterized by their expression of insulin and at least one of the following transcription factors: PDX1, NKX2.2, NKX6.1, NeuroD1, ISL1, HNF30, MAFA and PAX6.

The terms "stem cell-derived β cell" and "SC-β cell" are used interchangeably herein to refer to non-native cells differentiated in vitro (e.g., from pluripotent stem cells) that display at least one marker indicative of a pancreatic β cell (e.g., PDX-1 or NKX6-1), expresses insulin, and display a GSIS response characteristic of an endogenous mature β cell both in vitro and in vivo. The GSIS response of the SC-β cells can be observed within two weeks of transplantation of the SC-β cell into a host (e.g., a human or animal). It is to be understood that the SC-β cells need not be derived (e.g., directly) from stem cells, as the methods of the disclosure are capable of deriving SC-β cells from any endocrine progenitor cell that expresses insulin or precursor thereof using any cell as a starting point (e.g., one can use embryonic stem cells, induced-pluripotent stem cells, progenitor cells, partially reprogrammed somatic cells (e.g., a somatic cell which has been partially reprogrammed to an intermediate state between an induced pluripotent stem cell and the somatic cell from which it was derived), multipotent cells, totipotent cells, a transdifferentiated version of any of the foregoing cells, etc, as the invention is not intended to be limited in this manner). In some aspects, human cells are excluded that are derived from human embryonic stem cells obtained exclusively by a method necessitating the destruction of an embryo. The skilled artisan is well aware of such methods and how to avoid them for the purposes of generating SC-β cells according to the methods of the present invention.

Used interchangeably herein are "d1", "1d", and "day 1"; "d2", "2d", and "day 2", etc. These number letter combinations refer to a specific day of incubation in the different stages during the stepwise differentiation protocol of the instant application.

Methods for Generating SC-β Cells

Figure 3B:
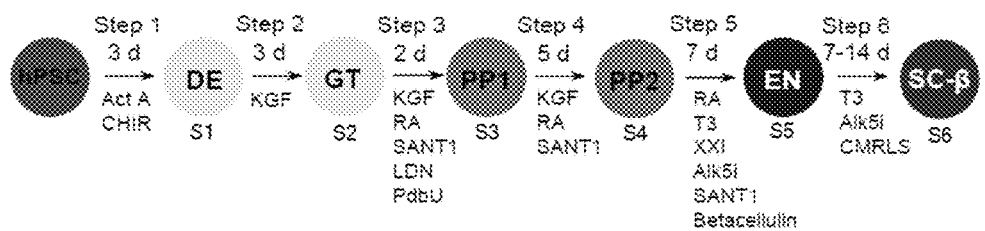
FIG. 3B is a schematic illustrating an exemplary six step differentiation protocol for generating SC-β cells from pluripotent stem cells, as described further in Pagliuca et al. 2014 and PCT International Application No. PCT/US2014/041992.

Recently, two protocols for directing the differentiation of pluripotent stem cells into insulin-producing endocrine cells that express key markers of mature pancreatic β cells (e.g., SC-β cells) have been reported, each of which includes differentiating cells into endocrine progenitor cells that can be directed to differentiate into SC-β cells as well as protocols for directing the pancreatic endocrine progenitor cells into SC-β cells, which can be used in the method disclosed herein for generating SC-β cells. First, as is shown in FIG. 3B, a six-stage protocol for the large-scale production of functional human β cells using human pluripotent stem cells (hPSC) by sequential modulation of multiple signaling pathways in a three-dimensional cell culture system, without using any transgenes or genetic modification, was used to generate glucose-responsive, monohormonal insulin-producing cells that exhibited key β cell markers and β cell ultrastructure (see Pagliuca et al., 2014 and PCT International Application No. PCT/US2014/041992, both of which are incorporated herein by reference in their entirety). Pagliuca and colleagues reported that such cells mimicked the function of human islets in vitro and in vivo, and demonstrated the potential utility of such cells for in vivo transplantation to treat diabetes. Secondly, a seven-stage protocol that converts human embryonic stem cells (hESCs) into insulin-producing cells that expressed key markers of mature pancreatic β cells, such as MAFA, and displayed glucose-stimulated insulin secretion like that of human islets using static incubations in vitro was described (Rezania et al., 2014). Cells produced by such protocol, referred to as S7 cells, were found to rapidly reverse diabetics in mice within a little over a month.

Figure 4A:
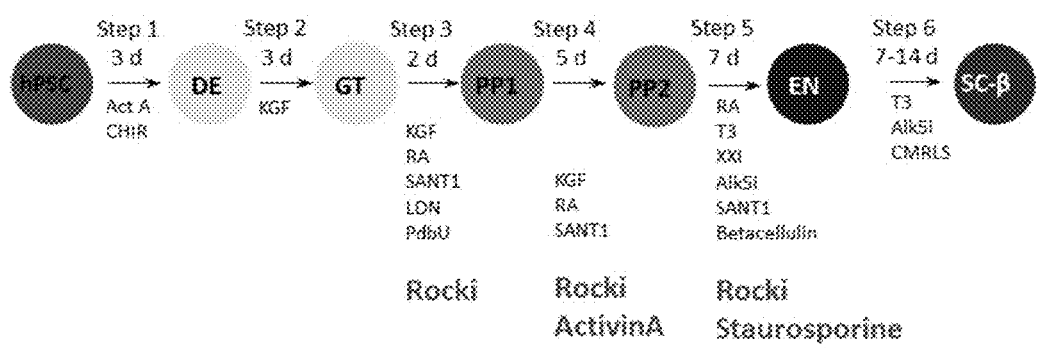
FIG. 4A is a schematic illustrating an exemplary method for generating SC-β cells according to an embodiment of the present invention, e.g., by contacting a cell population directed to differentiate to SC-β cells under conditions that promote cell clustering with an agent that decreases the level and/or activity of rho-associated protein kinase (Rock inhibitor), a TGF-β superfamily member (e.g., Activin A), and a protein kinase inhibitor (e.g., staurosporine) during the steps indicated.

FIG. 4A shows an exemplary method for generating SC-β cells in accordance with an embodiment of the present invention that results in larger cell clusters comprising greater numbers of SC-β cells exhibiting a more pure endocrine population and greater number of SC-β cells exhibiting co-expression of NKX6.1 and C-peptide.

In accordance with an example embodiment of the present invention, a method for generating stem cell-derived β (SC-β) cells comprises contacting a cell population directed to differentiate to SC-β cells under conditions that promote cell clustering with a) an effective amount of an agent that decreases the level and/or activity of rho-associated protein kinase (Rock) while the cell population comprises i) FOXA2+, SOX2+ primitive foregut cells differentiating to PDX1+ pancreatic progenitor cells, ii) PDX1+ pancreatic progenitor cells differentiating into PDX1+, NKX6.1+ pancreatic progenitor cells, and/or iii) PDX1+, NKX6.1+ pancreatic progenitor cells differentiating to chromogranin A, NKX6.1+ endocrine progenitor cells; b) an effective amount of a TGF-β superfamily member while the cell population comprises ii) PDX1+ pancreatic progenitor cells differentiating to PDX1+, NKX6.1+ pancreatic progenitor cells; and c) an effective amount of a protein kinase inhibitor while the cell population comprises iii) PDX1+, NKX6.1+ pancreatic progenitor cells differentiating to chromogranin A, NKX6.1+ endocrine progenitor cells, thereby generating SC-β cells.

"Contacting", "contacting the cell" and any derivations thereof as used herein, refers to any means of introducing an agent (e.g., nucleic acids, peptides, ribozymes, antibodies, small molecules, etc.) into a target cell or an environment in which the cell is present (e.g., cell culture), including chemical and physical means, whether directly or indirectly. Contacting also is intended to encompass methods of exposing a cell, delivering to a cell, or 'loading' a cell with an agent by viral or non-viral vectors, and wherein such agent is bioactive upon delivery. The method of delivery will be chosen for the particular agent and use. Parameters that affect delivery, as is known in the medical art, can include, inter alia, the cell type affected, and cellular location. In some aspects, contacting includes administering the agent to a subject. In some aspects, contacting refers to exposing a cell or an environment in which the cell is located (e.g., cell culture medium) to at least one agent that decreases the level and/or activity of Rock (also referred to herein as "ROCK inhibitor"). In some aspects, contacting refers to exposing a cell or an environment in which the cell is located (e.g., cell culture medium) to a TGF-β superfamily member (e.g., Activin A). In some aspects, contacting refers to exposing a cell or an environment in which the cell is located (e.g., cell culture medium) to a protein kinase inhibitor (e.g., staurosporine).

In accordance with aspects of the present invention, the method includes an optional step of washing the cell population after the PDX1+ pancreatic progenitor cells have differentiated to PDX1+, NKX6.1+ pancreatic progenitor cells to remove Activin A from contact with the cell population before contacting the cell population with staurosporine.

The methods of the present invention contemplate: i) contacting cells or cell populations (e.g., comprising S2, S3, and S4 cells) with an effective amount of one or more Rock inhibitors; ii) contacting cells or cell populations (e.g., comprising S3 cells) with an effective amount of a TGF-β superfamily member (e.g., Activin A); and iii) contacting cells or cell populations (e.g., comprising S4 cells) with an effective amount of a protein kinase inhibitor (e.g., staurosporine). An "effective amount" of an agent (or composition containing such agent) refers to the amount sufficient to achieve a desired effect, e.g., when delivered to a cell or subject according to a selected administration form, route, and/or schedule. As will be appreciated by those of ordinary skill in this art, the absolute amount of a particular agent or composition that is effective may vary depending on such factors as the desired biological or pharmacological endpoint, the agent to be delivered, the target tissue, etc. Those of ordinary skill in the art will further understand that an "effective amount" may be contacted with cells or administered in a single dose, or the desired effect may be achieved by use of multiple doses. An effective amount of a composition may be an amount sufficient to reduce the severity of or prevent one or more symptoms or signs of a disorder (e.g., diabetes). In some aspects, the effective amount of the agent that decreases the level and/or activity of ROCK comprises a concentration of between about 0.1 µM and about 110 µM. In some aspects, the effective amount of the agent (e.g., ROCK inhibitor) comprises 10 µM. In some aspects, the effective amount of the TGF-µ superfamily member comprises a concentration of between about 1 ng/ml to about 1000 ng/ml. In some aspects, the effective amount of the TGF-β superfamily member comprises 5 ng/ml. In some aspects, the effective amount of the protein kinase inhibitor comprises a concentration of between about 0.1 nM and 110 nM. In some aspects, the effective amount of the protein kinase inhibitor comprises a concentration of 3 nM.

The present invention contemplates using any agent that decreases the level and/or activity of ROCK in the methods for generating SC-β cells, e.g., ROCK inhibitors can be small organic or inorganic molecules; saccharides; oligosaccharides; polysaccharides; biological macromolecules, e.g., peptides, proteins, and peptide analogs and derivatives; peptidomimetics; nucleic acids and nucleic acid analogs and derivatives (including but not limited to microRNAs, siRNAs, shRNAs, antisense RNAs, a ribozymes, and aptamers); an extract made from biological materials such as bacteria, plants, fungi, or animal cells; animal tissues; naturally occurring or synthetic compositions; and any combinations thereof.

Exemplary ROCK inhibitors include, but are not limited to a small organic molecule ROCK inhibitor selected from the group consisting of N-[(1S)-2-Hydroxy-1-phenylethyl]-N'-[4-(4-pyridinyl)phenyl]-urea (AS1892802), fasudil hydrochloride (also known as HA 1077), -[3-[[2-(4-Amino-1,2,5-oxadiazol-3-yl)-1-ethyl-1H-imidazo[4,5-c]pyridin-6-yl]oxy]phenyl]-4-[2-(4-morpholinyl)ethoxy]benzamide (GSK269962), 4-[4-(Trifluoromethyl)phenyl]-N-(6-Fluoro-1H-indazol-5-yl)-2-methyl-6-oxo-1,4,5,6-tetrahydro-3-pyridinecarboxamide (GSK 429286), (5)-(+)-2-Methyl-1-[(4-methyl-5-isoquinolinyl)sulfonyl]-hexahydro-1H-1,4-diazepine dihydrochloride (H 1152 dihydrochloride), (S)-(+)-4-Glycyl-2-methyl-1-[(4-methyl-5-isoquinolinyl) sulfonyl]-hexahydro-1H-1,4-diazepine dihydrochloride (glycyl-H 1152 dihydrochloride), N-[(3-Hydroxyphenyl) methyl]-N'-[4-(4-pyridinyl)-2-thiazolyl]urea dihydrochloride (RKI 1447 dihydrochloride), (3S)-1-[[2-(4-Amino-1,2,5-oxadiazol-3-yl)-1-ethyl-1H-imidazo[4,5-c]pyridin-7-yl] carbonyl]-3-pyrrolidinamine dihydrochloride (SB772077B dihydrochloride), N-[2-[2-(Dimethylamino)ethoxy]-4-(1H-pyrazol-4-yl)phenyl-2,3-dihydro-1,4-benzodioxin-2-carboxamide dihydrochloride (SR 3677 dihydrochloride), and trans-4-[(1R)-1-Aminoethyl]-N-4-pyridinylcyclohexanecarboxamide dihydrochloride (Y-27632 dihydrochloride), N-Benzyl[2-(pyrimidin-4-yl)amino]thiazole-4-carboxamide (Thiazovivin), Rock Inhibitor, a isoquinolinesulfonamide compound (Rho Kinase Inhibitor), N-(4-Pyridyl)-N'-(2,4,6-trichlorophenyl)urea (Rho Kinase Inhibitor II), 3-(4-Pyridyl)-1H-indole (Rho Kinase Inhibitor III, Rockout), and 4-pyrazoleboronic acid pinacol ester; a Rock antibody commercially available from Santa Cruz Biotechnology selected from the group consisting of Rock-1 (B1), Rock-1 (C-19), Rock-1 (H-11), Rock-1 (G-6), Rock-1 (H-85), Rock-1 (K-18), Rock-2 (C-20), Rock-2 (D-2), Rock-2 (D-11), Rock-2 (N-19), Rock-2 (H-85), Rock-2 (30-J); a ROCK CRISPR/Cas9 knockout plasmid selected from the group consisting of Rock-1 CRISPR/Cas9 KO plasmid (h), Rock-2 CRISPR/Cas9 KO plasmid (h), Rock-1 CRISPR/Cas9 KO plasmid (m), Rock-2 CRISPR/Cas9 KO plasmid (m); a ROCK siRNA, shRNA plasmid and/or shRNA lentiviral particle gene silencer selected from the group consisting of Rock-1 siRNA (h): sc-29473, Rock-1 siRNA (m): sc-36432, Rock-1 siRNA (r): sc-72179, Rock-2 siRNA (h): sc-29474, Rock-2 siRNA (m): sc-36433, Rock-2 siRNA (r): sc-108088.

In some aspects, a ROCK inhibitor decreases the level and/or activity of ROCK in cells contacted by at least 5%, 10%, 20%, 30%, 40%, 50%, 60%, 70%, 80%, 90%, or 95% relative to the level or activity of ROCK in the cells in the absence of contact with the ROCK inhibitor. While not required, a ROCK inhibitor can completely inhibit the level and/or activity of ROCK in the cells. It should be appreciated that the ROCK inhibitors may decrease the level and/or activity of ROCK in any cell in the population in which the S2, S3 and/or S4 cells are differentiating, including endocrine progenitor cells in population, SC-β cells, and any precursors thereof.

In accordance with aspects of the present invention, the agent (e.g., ROCK inhibitor) comprises Y-27632.

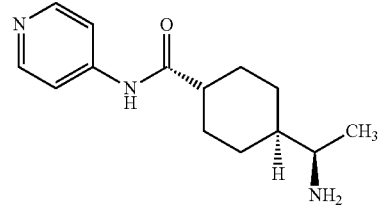

Y-27632

An effective amount of Y-27632 for use in the methods of the present invention can be, for example, between about 0.1 µM and about 110 µM. In some aspects, an effective amount of tY-27632 comprises 10 µM.

The present invention contemplates using any agent TGF-β superfamily member. Exemplary such members include, but are not limited to, Nodal, Activin A, Activin B, bone morphogenic protein-2 (BMP2), bone morphogenic protein-4 (BMP4) and functional fragments thereof. In accordance with aspects of the present invention, the TGF-β superfamily member comprises Activin A.

An effective amount of Activin A for use in the methods of the present invention can be, for example, between about 1 ng/ml to about 1000 ng/ml. In accordance with aspects of the present invention, an effective amount of Activin A comprises a concentration of 5 ng/ml.

The present invention contemplates using any protein kinase inhibitor that is capable of generating a near pure endocrine population or increasing the number of cells in the population coexpressing and NKX6.1+, C-peptide in the methods for generating SC-β cells.

In accordance with aspects of the present invention, the protein kinase inhibitor comprises staurosporine. An effective amount of staurosporine for use in the methods of the present invention can be, for example, between about 0.1 nM and about 110 nM. In accordance with aspects of the present invention, an effective amount of staurosporine comprises a concentration of 3 nM.

Figure 4B:
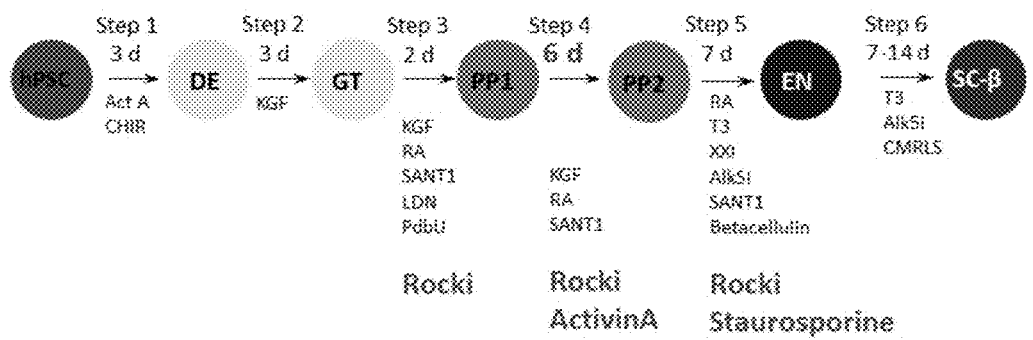
FIG. 4B is a schematic illustrating an exemplary method for generating SC-β cells according to an embodiment of the present invention, e.g., by contacting a cell population directed to differentiate to SC-β cells under conditions that promote cell clustering with an agent that decreases the level and/or activity of rho-associated protein kinase (Rock inhibitor), a TGF-β superfamily member (e.g., Activin A), and a protein kinase inhibitor (e.g., staurosporine) during the steps indicated, and in which Step 4 is carried out for an additional 24 hours compared to the method depicted in FIG. 4A.

In accordance with aspects of the present invention, as is shown in FIG. 4B, the cell population comprising ii) PDX1+ pancreatic progenitor differentiating to PDX1+, NKX6.1+ pancreatic progenitor cells is exposed to the agent and TGF-β superfamily member (e.g., Activin A) for a period of 6 days.

Preferably, a maximum number of cells in the population differentiate to chromogranin A, NKX6.1+ endocrine progenitor cells before differentiating into SC-β cells. The number of cells in the population differentiating to chromogranin A, NKX6.1+ endocrine progenitor cells before differentiating into SC-β cells is 5%, 10%, 15%, 20%, 25%, 30%, 40%, 45%, 50%, 55%, 60%, 65%, 70%, or more. In accordance with aspects of the present invention, between at least between 75% and 80% of the cell population differentiates to chromogranin A, NKX6.1+ endocrine progenitor cells before differentiating to SC-β cells.

SC-β Cells Obtained by the Method of Generating SC-β Cells

In accordance with an embodiment of the present invention, an isolated SC-β cell or population thereof generated according to a method described herein is provided. The isolated SC-β cell or population exhibits a GSIS response both in vitro and in vivo. The isolated SC-β cell or population also exhibits at least one characteristic feature of a mature endogenous β cell (e.g., monohormonality). In some aspects, an isolated SC-β cell or population thereof exhibits a stimulation index of between about 1.0 and about 3.0. In some aspects, an isolated SC-β cell or population thereof produces between approximately 300 uIU to about 4000 uIU per 30 minute per $10^6$ total cells incubation at a high glucose concentration.

The SC-β cells disclosed herein share many distinguishing features of native β cells, but are different in certain aspects (e.g., gene expression profiles). In some embodiments, the SC-β cell is non-native. As used herein, "non-native" means that the SC-β cells are markedly different in certain aspects from β cells which exist in nature, i.e., native β cells. It should be appreciated, however, that these marked differences typically pertain to structural features which may result in the SC-β cells exhibiting certain functional differences, e.g., although the gene expression patterns of SC-β cells differs from native β cells, the SC-β cells behave in a similar manner to native β cells but certain functions may be altered (e.g., improved) compared to native β cells. For example, a higher frequency of SC-β cells respond to 20 mM glucose compared to the frequency of native β cells. Other differences between SC-β cells and native β cells would be apparent to the skilled artisan based on the data disclosed herein.

The SC-β cells of the disclosure share many characteristic features of β cells which are important for normal β cell function. For example, the SC-β cells (e.g., human) generated according to the methods described herein may further exhibit at least one of the following characteristics of an endogenous mature pancreatic β cell: i) a response to multiple glucose challenges that resembles the response of endogenous islets (e.g., at least one, at least two, or at least three or more sequential glucose challenges); ii) a morphology that resembles the morphology of an endogenous β cell; iii) packaging of insulin into secretory granules or encapsulated crystalline insulin granules; iv) a stimulation index of greater than at least 1.4; v) cytokine-induced apoptosis in response to cytokines; vi) enhanced insulin secretion in response to known antidiabetic drugs (e.g., secretagogues); vii) monohormonal, i.e., they do not abnormally co-express other hormones, such as glucagon, somatostatin or pancreatic polypeptide; viii) a low rate of replication; and ix) increased intracellular $Ca^{2+}$ in response to glucose.

In accordance with an embodiment of the present invention, a microcapsule comprising the isolated SC-β cell or population thereof encapsulated therein is provided.

In accordance with an embodiment of the present invention, a macroencapsulation device comprising the isolated SC-β cell or population thereof is provided.

In accordance with an embodiment of the present invention, a cell line comprising an isolated SC-β cell that stably expresses insulin is provided.

Assays

In accordance with an embodiment of the present invention, an isolated SC-β cell or population thereof generated according to the methods herein, or an SC-β cell that stably expresses insulin, can be used in various assays. In some aspects, an isolated SC-β cell, population thereof, or an SC-β cell that stably expresses insulin, can be used in an assay to identify one or more candidate agents which promote or inhibit a β cell fate selected from the group consisting of β cell proliferation, β cell replication, β cell death, β cell function, β cell susceptibility to immune attack, and β cell susceptibility to dedifferentiation or differentiation. In some aspects, an isolated SC-β cell, population thereof, or an SC-β cell that stably expresses insulin, can be used in an assay to identify one or more candidate agents which promote the differentiation of at least one insulin-positive endocrine cell or a precursor thereof into at least one SC-β cell. The assays typically involve contacting the isolated SC-β cell, population thereof, or an SC-β cell that stably expresses insulin, with one or more candidate agents to be assessed for its ability to i) promote or inhibit a β cell fate selected from the group consisting of β cell proliferation, β cell replication, β cell death, β cell function, β cell susceptibility to immune attack, and β cell susceptibility to dedifferentiation or differentiation, or ii) promoting the differentiation of at least one insulin-positive endocrine cell or a precursor thereof into at least one SC-β cell and assessing whether the candidate agent possesses the ability to i) promote or inhibit a β cell fate selected from the group consisting of β cell proliferation, β cell replication, β cell death, β cell function, β cell susceptibility to immune attack, and β cell susceptibility to dedifferentiation or differentiation, or ii) promoting the differentiation of at least one insulin-positive endocrine cell or a precursor thereof into at least one SC-β cell.

Methods for Treatment

In accordance with an embodiment of the present invention, methods for the treatment of a subject in need thereof are provided. The methods entail administering to a subject in need thereof an isolated population of SC-β cells or a microcapsule comprising SC-β cells encapsulated therein. In some aspects, the subject is in need of additional β cells. In some aspects, the subject has, or has an increased risk of developing diabetes, A SC-β cell or population (e.g., isolated) of SC-β cells generated by a method of the present invention can be administered to a subject for treatment of type 1 or type 2 diabetes. In some aspects, the subject has, or has an increased risk of developing, a metabolic disorder. In some aspects, administering to the subject comprises implanting SC-β cells, a microcapsule comprising SC-β cells, or a macroencapsulation device comprising SC-β cells into the subject. The subject may be a human subject or an animal subject. In some aspects, the cells may be implanted as dispersed cells or formed into clusters that may be infused into the hepatic portal vein. In some aspects, cells may be provided in biocompatible degradable polymeric supports, porous non-degradable devices or encapsulated to protect from host immune response. Cells may be implanted into an appropriate site in a recipient. The implantation sites include, for example, the liver, natural pancreas, renal subcapsular space, omentum, peritoneum, subserosal space, intestine, stomach, or a subcutaneous pocket.

To enhance further differentiation, survival or activity of the implanted cells in vivo, additional factors, such as growth factors, antioxidants or anti-inflammatory agents, can be administered before, simultaneously with, or after the administration of the cells. These factors can be secreted by endogenous cells and exposed to the administered cells in situ. Implanted cells can be induced to differentiate by any combination of endogenous and exogenously administered growth factors known in the art.

The amount of cells used in implantation depends on a number of various factors including the patient's condition and response to the therapy, and can be determined by one skilled in the art.

In some aspects, the method of treatment further comprises incorporating the cells into a three-dimensional support prior to implantation. The cells can be maintained in vitro on this support prior to implantation into the patient. Alternatively, the support containing the cells can be directly implanted in the patient without additional in vitro culturing. The support can optionally be incorporated with at least one pharmaceutical agent that facilitates the survival and function of the transplanted cells.

Artificial Islet or Pancreas

In accordance with an embodiment of the present invention, an artificial islet or pancreas is provided. The artificial islet or pancreas can be constructed using the SC-β cells generated according to the methods described herein.

An artificial pancreas is a device that encapsulates and nurtures islets of Langerhans to replace the islets and β cells destroyed by type 1 diabetes. An artificial pancreas may contain a million islets or more, and may be implanted in the peritoneal cavity or under the skin where it can respond to changing blood glucose levels by releasing hormones, such as insulin. An artificial pancreas may be made using living (e.g., glucose-sensing and insulin secreting islets) and non-living components (e.g., to shield the islets from the diabetic's body and its destructive immune mechanism while permitting the islets to thrive).

The present invention contemplates using β cells in any artificial pancreas. In some aspects, the artificial pancreas comprises microencapsulated or coated islets comprising SC-β cells generated according to the methods herein. In some aspects, the artificial pancreas comprises a macroencapsulation device into which islet cells comprising SC-β cells generated according to the methods herein are grouped together and encapsulated. In some aspects, the macroencapsulation device comprises a PVA hydrogel sheet for an artificial pancreas of the present invention (Qi et al., 2004). In some aspects, the artificial islet comprises SC-β cells generated according to the methods herein, along with other islet cells (α, δ, etc.) in the form of an islet sheet. The islet sheet comprises a layer of artificial human islets comprising the SC-β cells macroencapsulated within a membrane (e.g., of ultra-pure alginate). The sheet membrane is reinforced with mesh and may be coated on the surface to prevent or minimize contact between the cells encapsulated inside and the transplantation recipient's host immune response. Oxygen, glucose, and other nutrients readily diffuse into the sheet through the membrane nurturing the islets, and hormones, such as insulin readily diffuse out. Additional examples of membranes designed for macroencapsulation/implantation of an artificial islet or pancreas can be found in the literature (Isayeva et al. 2003). Another example of a macroencapsulated implant suitable for an artificial islet or pancreas can be found in the literature (Aurélien, et al. 2014).

Terminology

The articles "a", "an" and "the" as used herein, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in haec verba herein. It should also be understood that any embodiment of the invention, e.g., any embodiment found within the prior art, can be explicitly excluded from the claims, regardless of whether the specific exclusion is recited in the specification. For example, any agent may be excluded from the genera of ROCK inhibitors, TGF-β superfamily members, and protein kinase inhibitors.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" generally includes numbers that fall within a range of 1% or in some embodiments 5% of a number in either direction (greater than or less than the number) unless otherwise stated or otherwise evident from the context (except where such number would impermissibly exceed 100% of a possible value).

Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, e.g., in Markush group or similar format, it is to be understood that each subgroup of the elements is also disclosed, and any element(s) can be removed from the group.

Certain claims are presented in dependent form for the sake of convenience, but any dependent claim may be rewritten in independent format to include the limitations of the independent claim and any other claim(s) on which such claim depends, and such rewritten claim is to be considered equivalent in all respects to the dependent claim (either amended or unamended) prior to being rewritten in independent format. It should also be understood that, unless clearly indicated to the contrary, in any methods claimed herein that include more than one act, the order of the acts of the method is not necessarily limited to the order in which the acts of the method are recited, but the invention includes embodiments in which the order is so limited. It is contemplated that all aspects described above are applicable to all different embodiments of the invention. It is also contemplated that any of the above embodiments can be freely combined with one or more other such embodiments whenever appropriate.

REFERENCES

1. Bellin et al., (2012). Potent induction immunotherapy promotes long-term insulin independence after islet transplantation in type 1 diabetes. Am. J. Transplant. 12, 1576-1583.
2. Pagliuca et al. (2014). Generation of Functional Human Pancreatic β cells In Vitro. Cell. 159, 428-439.
3. Rezania et al. (2014). Reversal of diabetes with insulin-producing cells derived in vitro from human pluripotent stem cells. Nat. Biotech. 32(11), 1121-1133.
4. Isayeva, et al. (2003). Characterization and performance of membranes designed for macroencapsulation/implantation of pancreatic islet cells. Biomaterials 24(20), 3483-3491.
5. Motté, et al. (2014). Composition and function of macroencapsulated human embryonic stem cell-derived implants: comparison with clinical human islet cell grafts. American Journal of Physiology-Endocrinology and Metabolism 307(9), E838-E846.
6. Qi et al. (2004). PVA hydrogel sheet macroencapsulation of the bioartificial pancreas. *Biomaterials* 24(27), 5885-5892

What is claimed is:

1. A method comprising contacting a cell population comprising PDX1+ pancreatic progenitor cells that do not express NKX6.1 with a culture medium comprising rho-associated protein kinase (Rock) inhibitor and Activin A, wherein the contacting results in one or more cells in the cell population differentiating to PDX1+ pancreatic progenitor cells that express NKX6.1.

2. The method of claim 1, further comprising washing the cell population after the PDX1+ pancreatic progenitor cells that do not express NKX6.1 have differentiated to PDX1+ pancreatic progenitor cells that express NKX6.1, wherein said washing is effective to remove Activin A from contact with the cell population.

3. The method of claim 1, wherein the Rock inhibitor comprises Y-27632.

4. The method of claim 1, wherein the culture medium comprises 10 μM of the Rock inhibitor.

5. The method of claim 1, wherein the culture medium comprises 5 ng/ml of Activin A.

6. The method of claim 1, wherein the cell population comprising PDX1+ pancreatic progenitor cells that do not express NKX6.1 is exposed to the Rock inhibitor and Activin A for a period of 6 days.

7. The method of claim 1, wherein the method further i) prevents or minimizes cell cluster disintegration, ii) promotes cell survival, iii) increases number of PDX1+ pancreatic progenitor cells that express NKX6.1 in resulting cell population, and combinations thereof.

8. A method comprising contacting a cell population comprising PDX1+, NKX6.1+ pancreatic progenitor cells with a culture medium comprising rho-associated protein kinase (Rock) inhibitor and staurosporine, wherein the contacting results in one or more cells in the cell population differentiating to chromogranin A, NKX6.1+ endocrine progenitor cells.

9. The method of claim 8, further comprising differentiating the chromogranin A, NKX6.1+ endocrine progenitor cells to SC-β cells, wherein the SC-β cells exhibit co-expression of NKX6.1 and C-peptide.

10. The method of claim 8, wherein the culture medium comprises 3 nM of staurosporine.

11. The method of claim 8, wherein between at least 75% and 80% of the cell population differentiates to chromogranin A, NKX6.1+ endocrine progenitor cells before differentiating to SC-β cells.

* * * * *